United States Patent
Kesaniemi et al.

(10) Patent No.: US 11,253,162 B2
(45) Date of Patent: Feb. 22, 2022

(54) METHOD AND SYSTEM FOR HEART RATE ESTIMATION

(71) Applicant: GE Precision Healthcare LLC, Wauwatosa, WI (US)

(72) Inventors: Martti Ilmari Kesaniemi, Helsinki (FI); Rene Johannes Cornelis Coffeng, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 164 days.

(21) Appl. No.: 16/437,186

(22) Filed: Jun. 11, 2019

(65) Prior Publication Data
US 2020/0390351 A1    Dec. 17, 2020

(51) Int. Cl.
*A61B 5/024* (2006.01)
*A61B 5/0205* (2006.01)
(Continued)

(52) U.S. Cl.
CPC ........ *A61B 5/02405* (2013.01); *A61B 5/0205* (2013.01); *A61B 5/0245* (2013.01);
(Continued)

(58) Field of Classification Search
CPC . A61B 5/02405; A61B 5/0205; A61B 5/0245; A61B 5/0816; A61B 5/7207; A61B 5/02444; A61B 2562/0219
See application file for complete search history.

(56) References Cited

U.S. PATENT DOCUMENTS 7,937,135 B2 * 5/2011 Ghanem ............. A61N 1/3925
600/509
8,668,644 B2 * 3/2014 Ong ........................ G06N 3/04
600/301

(Continued)

FOREIGN PATENT DOCUMENTS

EP            0776631 B1 *  7/2003  ........... A61B 5/7203

OTHER PUBLICATIONS

Boudet G, Garet M, Bedu M, Albuisson E, Chamoux A. "Median maximal heart rate for heart rate calibration in different conditions: laboratory, field and competition." Int J Sports Med. May 2002;23(4):290-7. doi: 10.1055/s-2002-29081. PMID: 12015631. (Year: 2002).*

(Continued)

*Primary Examiner* — Mallika D Fairchild
*Assistant Examiner* — Shreya Anjaria
(74) *Attorney, Agent, or Firm* — Andrus Intellectual Property Law, LLP

(57) ABSTRACT

A computer-implemented method of heart rate estimation includes receiving heart beat data, detecting sequential beats within the heart beat data, identifying a beat interval of each sequential beat, and generating a beat array containing the beat intervals of sequential beats within an array window. The beat array is then sorted based on the beat intervals of the sequential beats so as to generate a sorted beat array. A weight array is calculated by applying a weight control parameter to each beat interval in the sorted beat array, wherein the weight array includes a weight value for each beat interval that is proportional to a corresponding beat interval value in the sorted beat array. A weighted median is calculated based on the weight array, and a heart rate estimation for the array window is determined based on the (Continued)

weighted median of the weight array and the sorted beat array.

21 Claims, 18 Drawing Sheets

(51) Int. Cl.
    *A61B 5/0245*     (2006.01)
    *A61B 5/08*     (2006.01)
    *A61B 5/00*     (2006.01)

(52) U.S. Cl.
    CPC ......... *A61B 5/02444* (2013.01); *A61B 5/0816* (2013.01); *A61B 5/7207* (2013.01); *A61B 2562/0219* (2013.01)

(56) References Cited

U.S. PATENT DOCUMENTS

| | | | | |
|---|---|---|---|---|
| 2005/0159667 A1* | 7/2005 | Korzinov | ............... | A61B 5/361 600/516 |
| 2007/0249949 A1* | 10/2007 | Hadley | ................. | G16H 50/30 600/519 |
| 2008/0027341 A1* | 1/2008 | Sackner | ................. | A61B 5/318 600/509 |
| 2011/0270102 A1* | 11/2011 | Zhang | ................ | A61N 1/36514 600/512 |
| 2019/0110755 A1* | 4/2019 | Capodilupo | ......... | G06K 9/6282 |

OTHER PUBLICATIONS

Suoranta, R and Estola, K. "Robust median filter with adaptive window length." IEEE International Symposium on Circuits and Systems, Singapore, 1991, pp. 108-111 vol. 1, doi: 10.1109/ISCAS.1991.176285. (Year: 1991).*

Risto Suoranta et al., Robust Median Filter with Adaptive Window Length, Machine Automation Laboratory, Technical Research Centre of Finland, 4 pages, 1991.

* cited by examiner

METHOD AND SYSTEM FOR HEART RATE ESTIMATION

BACKGROUND

This disclosure generally relates to period estimation for semi-periodic or quasi-periodic data, and more particularly to a method and system for period estimation in physiologic or other patient monitoring data.

Period estimation is performed for many types of physiologic or other patient monitoring data, such as cardiac signals and respiratory signals, and even motion signals (such as for counting/monitoring steps). In ECG monitoring, for example, heart rate is typically approximated based on detected heartbeat intervals. A heartbeat interval, or period, may be detected, for example, as the interval between sequential R waves (RR-interval) or the interval between sequential P waves (PP-interval). The heart rate calculation is then performed based on several intervals. Typically, the heart rate is calculated as a mean or a median of the beat intervals in the data set. With perfect, noiseless ECG or other heart beat data, the mean provides a more accurate representation of heartbeat. However, heart rate measurement is typically very noisy, and thus the mean calculation is unreliable because it is heavily influenced by the presence of noise and incorrectly measured RR or PP intervals. Thus, a median calculation is often used for estimating heart rate, where the middle value in a sorted set of intervals (e.g. sorted in ascending or descending order) is used as the heart rate estimation.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

On embodiment of a computer-implemented method of heart rate estimation includes receiving heart beat data, detecting sequential beats within the heart beat data, identifying a beat interval of each sequential beat, and generating a beat array containing the beat intervals of sequential beats within an array window. The beat array is then sorted based on the beat intervals of the sequential beats so as to generate a sorted beat array. A weight array is calculated by applying a weight control parameter to each beat interval in the sorted beat array, wherein the weight array includes a weight value for each beat interval that is proportional to a corresponding beat interval value in the sorted beat array. A weighted median is calculated based on the weight array, and a heart rate estimation for the array window is determined based on the weighted median of the weight array and the sorted beat array.

A patient monitoring system for monitoring heart rate includes at least two ECG electrodes configured to record at least one lead of heart beat data from a patient, and a software module (herein referred to as a "heart rate estimation module") executable to generate a beat array containing beat intervals of sequential beats within an array window of the heart beat data and then sort the beat array based on the beat intervals of the sequential beats to generate a sorted beat array. A weight array is calculated by applying a weight control parameter to each beat interval in the sorted beat array, wherein the weight array includes a weight value for each beat interval that is proportional to a corresponding beat interval value in the sorted beat array. A weighted median is calculated based on the weight array, then a heart rate estimation is determined for the array window based on the weighted median of the weight array and the sorted beat array.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
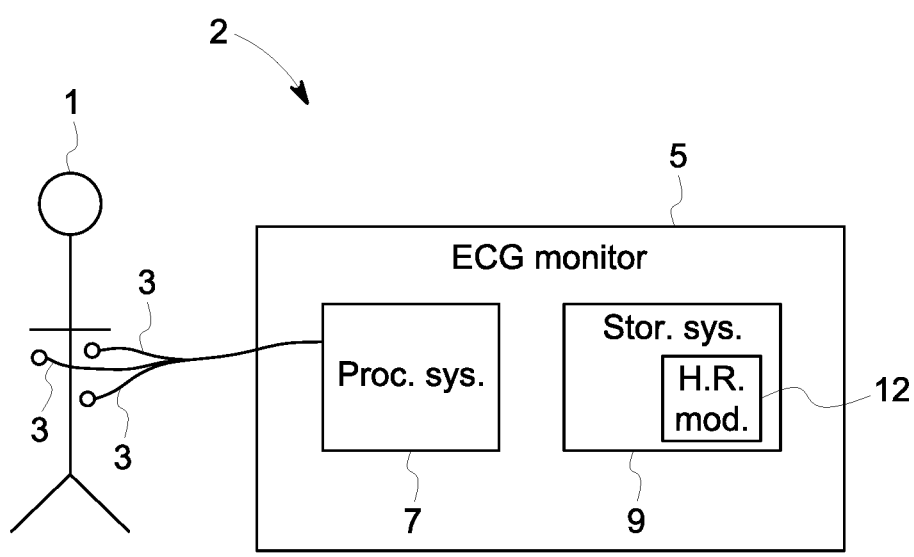
FIG. 1 depicts one embodiment of a system for monitoring heart rate.

FIG. 1 schematically depicts an ECG system 2 obtaining and processing heart beat data, exemplified here as ECG data, from a patient 1. In other embodiments, the system may detect pulse rate in SpO2 data or other types of data where heart beat is detectable. Electrodes 3 are attached to the patient and are sensing cardiac potentials, which get transmitted to the ECG monitor 5. Such an arrangement is conventional, and various numbers and configurations of electrodes 3 are well-known for obtaining ECG data from a patient 1. The ECG monitor includes a processing system 7 comprising one or more processors and circuitry for interfacing with a storage system 9 storing computer-executable software instructions. In the depicted example, the storage system 9 comprises a heart rate estimation module 12 comprising computer-executable instructions for estimating heart rate based on ECG data. In other embodiments, the heart rate estimation module 12 may be stored and executed elsewhere, such as stored and executed within a network or cloud-based computing system where ECG data is being processed.

As discussed below, embodiments of the method and computer software algorithm described herein may be adapted and applied to execute period estimation for other types of physiologic data, in addition to heart rate estimation based on ECG or other heart beat data, including for respiration rate estimation based on respiration data, for peak airway pressure estimation based on airway pressure measurements, and for gate or step frequency based on accelerometer or other motion data. Thus, in other embodiments, the heart rate estimation module may instead be a respiration rate estimation module, a peak pressure estimation module, or a step rate estimation module, and the system will incorporate corresponding physiological sensors and physiological monitoring devices.

The inventors have recognized that an improved heart rate estimation method is needed because current heart rate estimation systems utilizing median heart rate result in systematic error, especially in situations relating to high heart rate and/or for noisy heart beat data where erroneous beat detection occurs. FIGS. 2A-2E illustrate the problem with standard median heart rate detection. The graphs show exemplary heart rate estimations for exemplary heart rate data where the heart rate suddenly decreases from about 80 beats per minute (bpm) to about 40 bpm at time td. Heart rate estimations via standard mean and median calculation methods are illustrated. A window length of 16 seconds is used and the heart rate estimation is reperformed once per second. As can be seen, the mean calculation shows an immediate yet slow decrease over time, reflecting the true heart rate at about 34 seconds. The median is biased by existing data and thus provides a delayed response to the heart rate decrease, where the median response suddenly decreases from 80 to 40 at about 28 seconds.

Figure 2A:
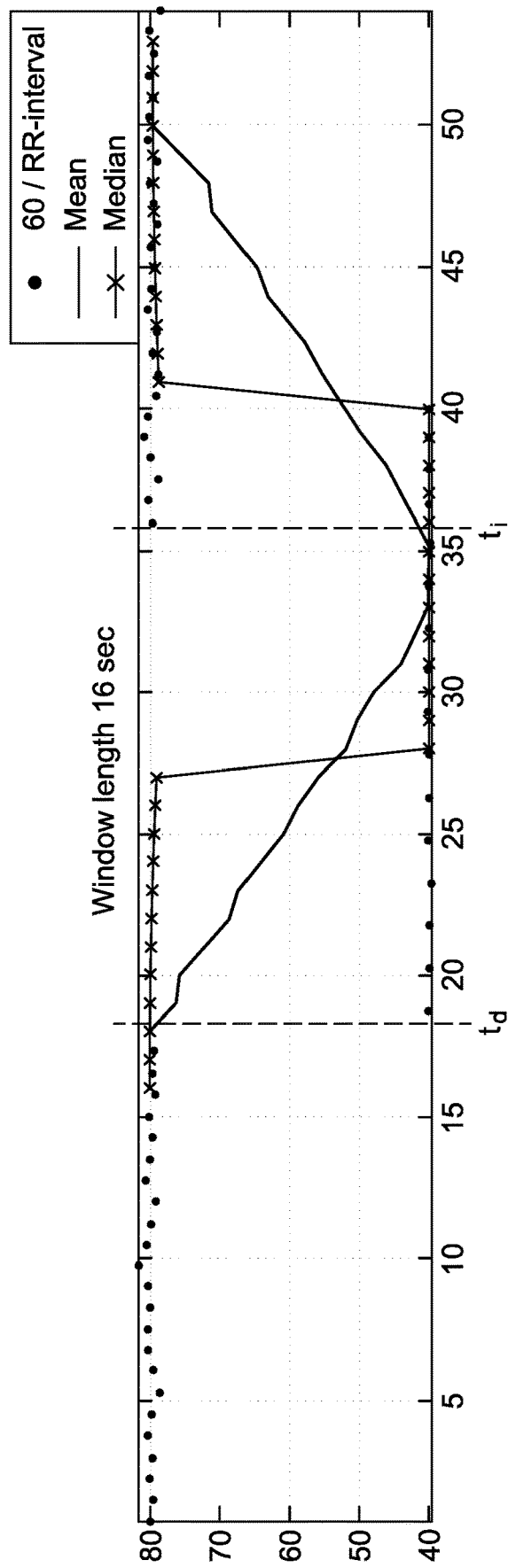
FIGS. 2A-2E are graphs comparing mean and median heart rate calculations for a given dataset.
Figure 2B:
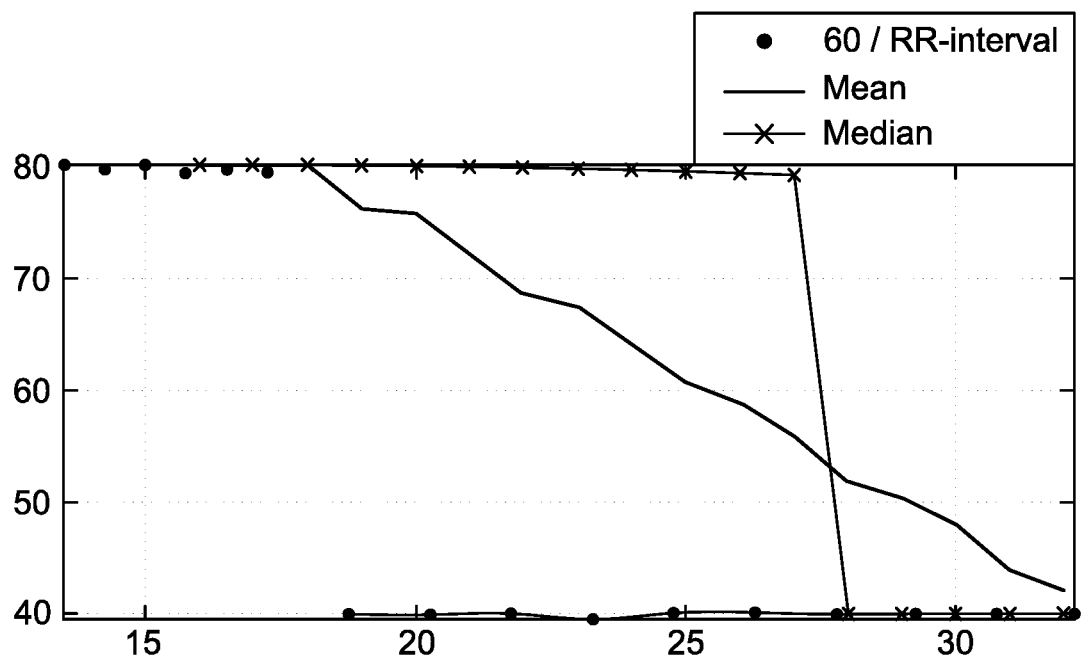
Figure 2C:
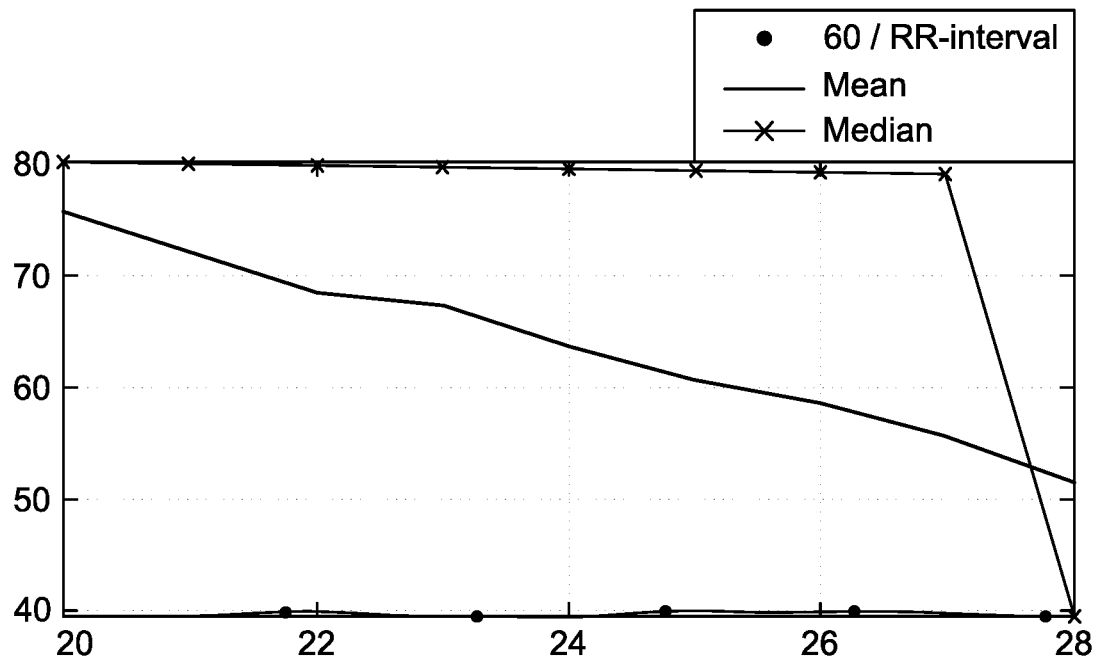

FIGS. 2B and 2C provide a zoomed-in view of the change in the median heart rate calculation. While the response in the median calculation from 80 to 40 takes approximately 10 seconds using the window length of 16 seconds, the response is significantly faster when the heart rate suddenly increases from 40 back to 80 bpm. The increase occurs at time ti, which is at about 36 seconds, and the mean heart rate calculation responds at about 41 seconds. This yields a bias, where the median calculation responds faster to a heart rate increase than to a heart rate decrease, and thus stays disproportionately higher compared to the data set and yields a disproportionality high average heart rate calculated over time (see FIG. 2E), for example.

Moreover, the median is not very responsive, especially to heart rate decreases, and thus does not provide accurate heart rate information in instances of significant changes in heart rate. For example, the median calculation may be insufficient to meet standards set for medical monitoring devices that monitor heart rate. As shown in the graph, for instance, the median heart rate calculation method is insufficient to meet the standard requirement that the heart rate estimation reflect a heart rate drop from 80 bpm to 40 bpm within 10 seconds.

Figure 2D:
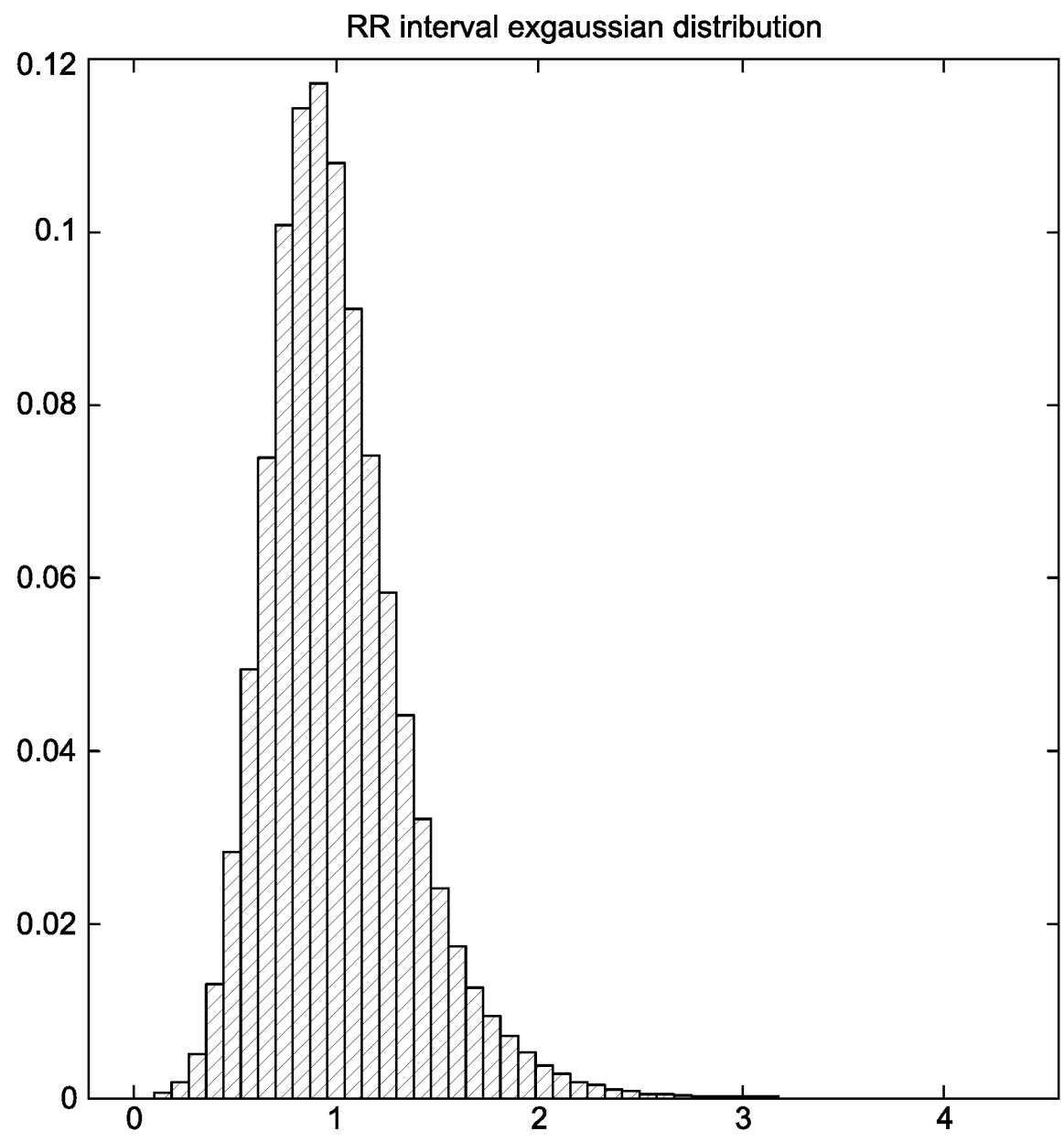
Figure 2E:
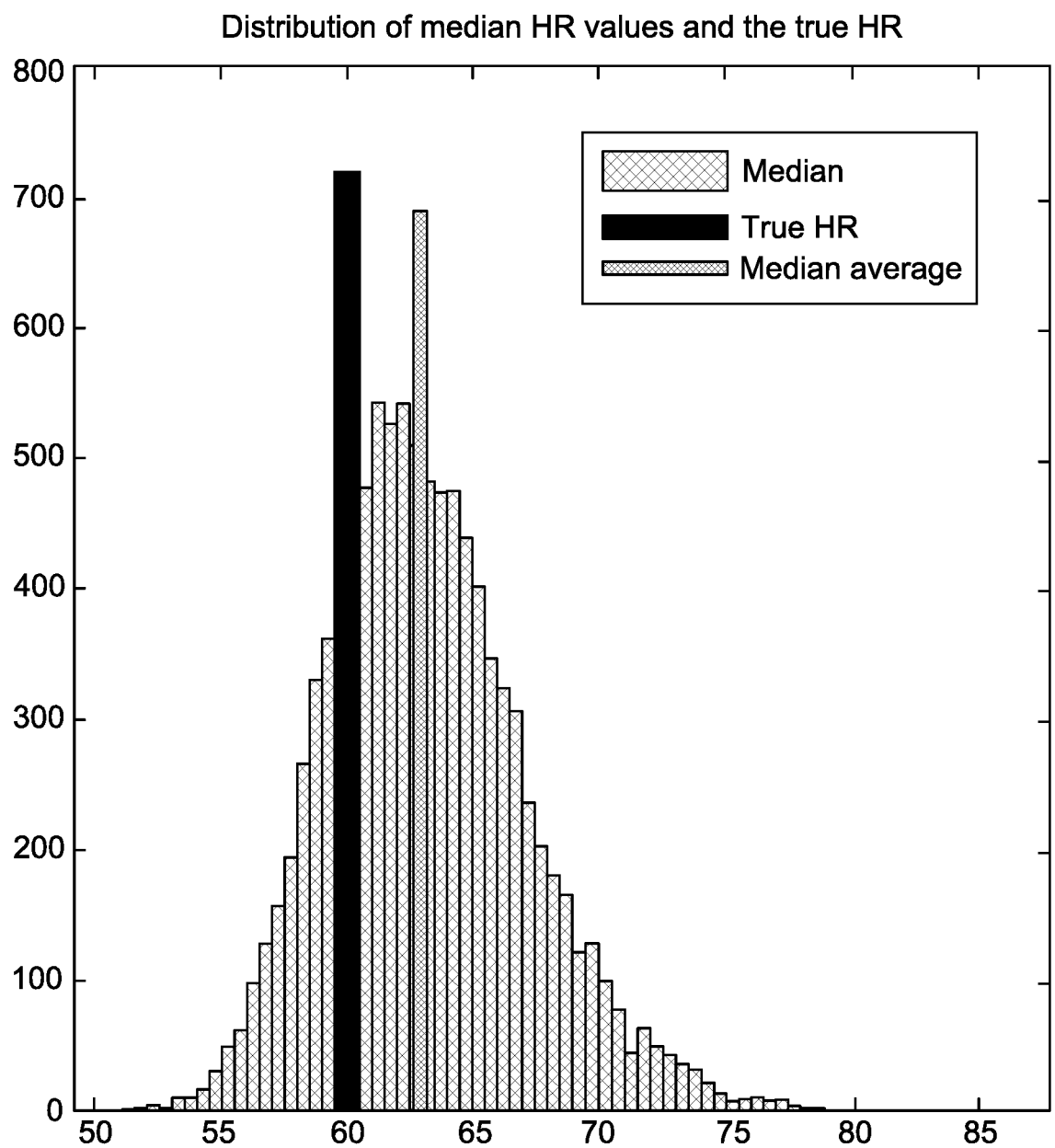

FIGS. 2D-2E illustrates the high heart rate bias, showing the median and median average calculations for RR interval data having an exponentially modified Gaussian (ex-Gaussian) distribution (FIG. 2D). FIG. 2E shows distributions of the heart rate values calculated using the beat interval data depicted in FIG. 2D, which shows that the median heart rate distribution is biased toward reflecting a higher heart rate than the true heart rate. In the example, the true average heart rate is 60 bpm, whereas the average median heart rate is about 62. In other words, on average, the median calculation gives a higher estimated heart rate than the true heart rate value.

Figure 3:
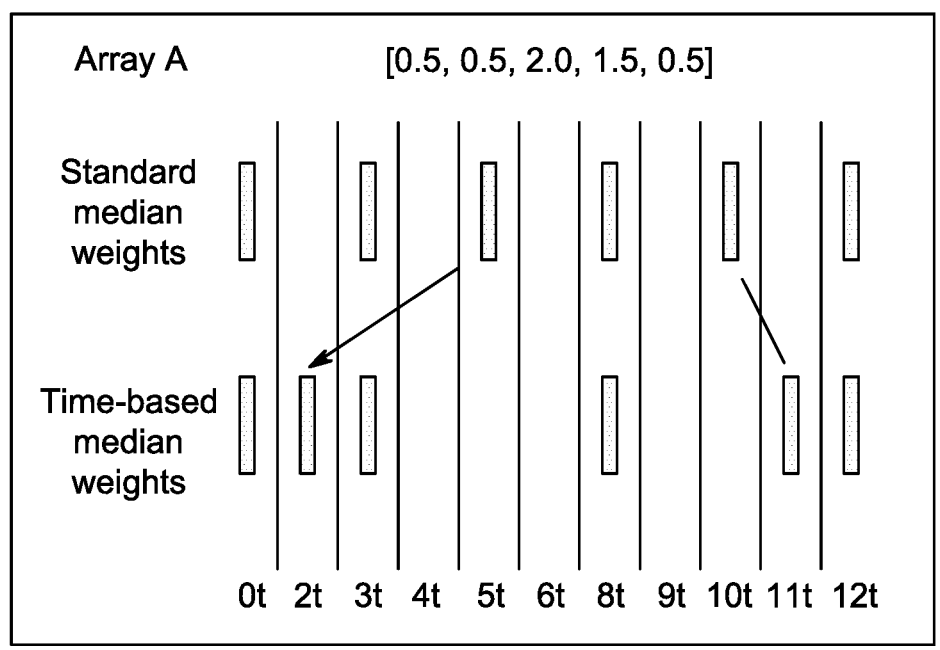
FIG. 3 schematically depicts a standard median calculation and a time-based median calculation.

One reason for this is because the median calculation weighs each beat interval equally, where long beat intervals get the same weight in the median window as short beat intervals. FIG. 3 demonstrates this point, where the standard median calculation method weighs every value in the array equally. In the example, Array A is an array of 6 intervals, which may be heart beat intervals. Using standard median method, each interval is weighed equally, thus the interval of two seconds between beats 2 and 3 is weighted equally with those intervals that are only 0.5 seconds.

Figure 4:
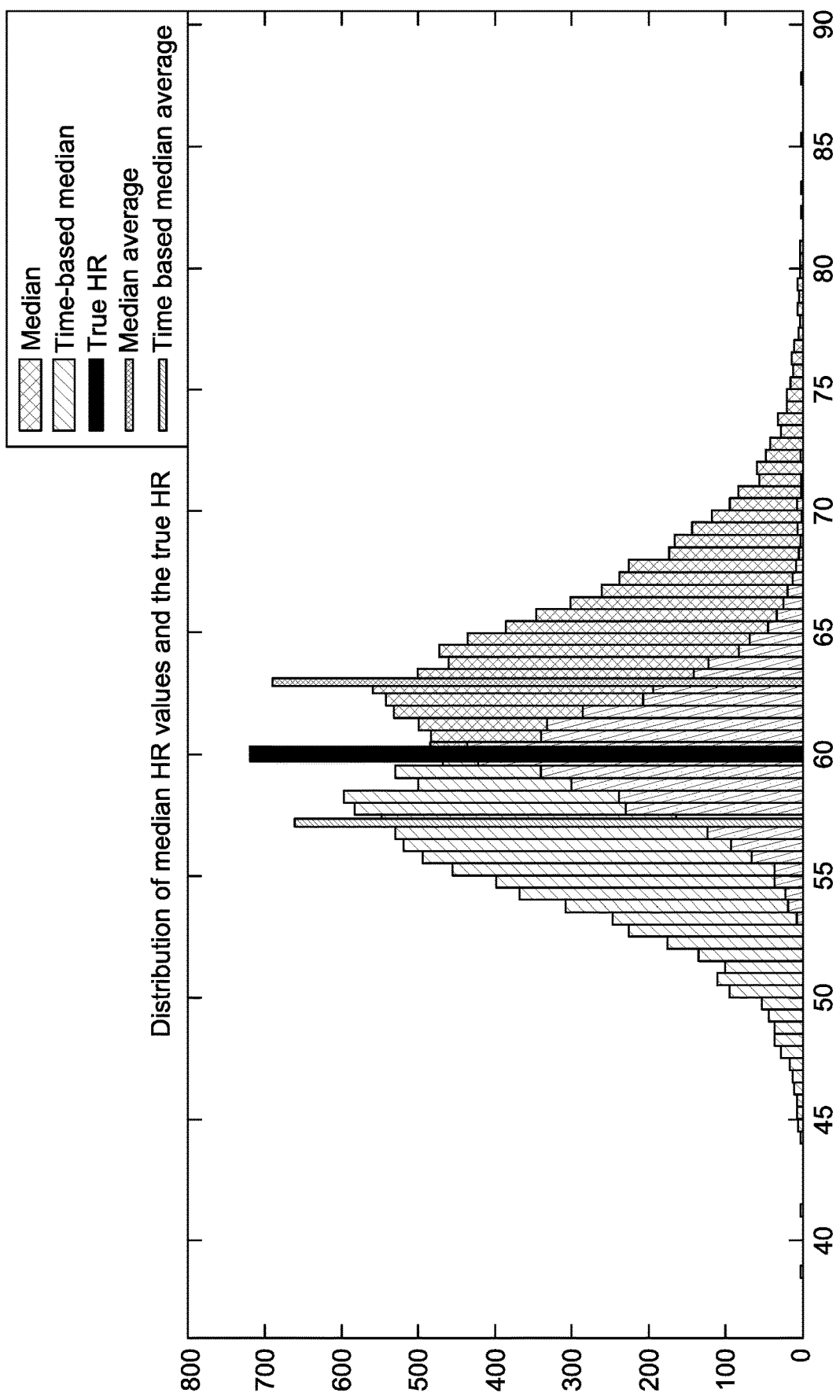
FIG. 4 is a graph comparing results of a time-based median heart rate calculation to a standard median heart rate calculation.

In the course of their research, the inventors explored a time-median heart rate determination by using a time-based median calculation, where the weight of each beat interval is directly proportional to the interval value itself. This is graphically illustrated in the bottom row of FIG. 3, where the time-based median weights are divided by equal time units (n*t) according to the duration of the beat interval. Thus, the beat interval of two seconds is weighed four times as much as the beat interval of 0.5 seconds. However, the inventors recognized that this time-based median method also presents bias issues and inaccuracies, though in an opposite direction than the bias resulting from the standard median calculation. FIG. 4 depicts a comparison between the time-based median calculation and the standard median calculation reflected in FIG. 2E. As shown, the time-based median calculation where the weight of each beat interval is directly proportional to the interval value, itself, results in a lower average heart rate calculation than the true heart rate. Thus, this time-based median method presents an opposite bias problem than the standard median calculation.

Accordingly, the inventors endeavored to adapt the time-based median calculation in order to develop a more accurate estimation of heart rate, herein referred to as the "T-median" calculation. The disclosed T-median heart rate estimation method developed by the inventors uses a weight control parameter in order to calculate a weight array, wherein the weight array includes a weight value for each beat interval that is proportional to, though not directly equal to, the beat interval value, itself. The weight of each beat interval is proportional to the interval value according to a function w=w(r), where r is the beat interval and w is the corresponding weight. Here, w(r) is an increasing function where the first derivative is greater than or equal to zero and the second derivative is zero or negative. In one embodiment, the weight function is provided by the following:

$$w(r)=r^{\lambda}, \text{ where } 0 \leq \lambda \leq 1 \qquad (1)$$

where λ represents the weight control parameter. Thus, each weight values is calculated as the beat interval raised to the power λ. Note that when λ=0, the calculated weighted time-median is the same as the standard median calculation, where each interval is weighted equally and the weight is equal to 1. When λ=1, the T-median weight equals the time-based median where the weight of each beat interval is directly proportional to the duration of the interval, itself (see FIG. 3).

Using this weight equation, a weight array is calculated that contains a weight value for each beat interval that is proportional to that corresponding beat interval value. Accordingly, the control parameter λ is used to adjust the time-based median calculation described above. Specifically, the T-median weight array $\omega_\lambda$ becomes $$\omega_\lambda = \omega_0{}^\lambda = [r_0, r_1 r_2 \ldots r_n]^\lambda \quad (2)$$

where $\omega_0$ is the array containing beat intervals and $\lambda$ is the control parameter. Thereby, the beat intervals are weighted according to a factor of their duration, where the factor is dictated by the weight control parameter.

As described herein, the weight control parameter can be adjusted up or down between zero and one based on the beat intervals being examined. Additionally, in some embodiments, the length of the array window can be adjusted in order to provide increased responsiveness in times of heart rate fluctuation. Accordingly, the disclosed method is not only more accurate than the existing standard median heart rate calculation, but is also more robust.

Figure 5:
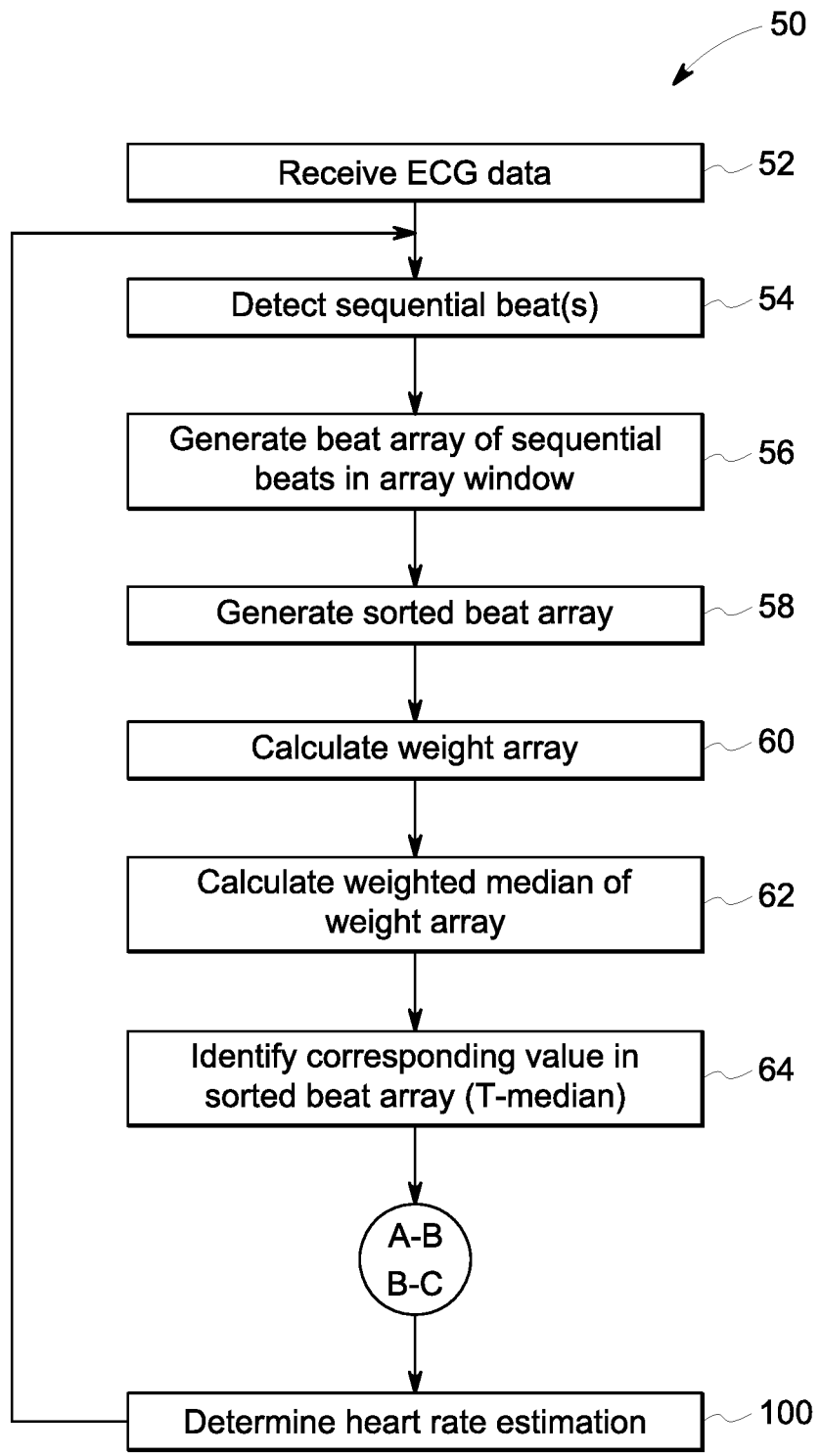
FIG. 5 is a flow chart illustrating a method of heart rate estimation according to one embodiment of the present disclosure.

FIG. 5 depicts one embodiment of a method 50 of heart rate estimation based on heart beat data. ECG data is received step 52 and sequential beats are detected within the ECG data at step 54. A beat array is generated at step 56 containing beat intervals of sequential beats within an array window, such as a predetermined period of time or a predetermined number of beats. In the context of ECG data, the beat intervals may be defined by, for example, the RR-interval or the PP-interval. In other embodiments, the disclosed period estimation algorithm may be utilized with different physiological data or patient monitoring data, such as for peak airway pressure estimation based on airway pressure data, respiration rate estimation based on respiration data, step frequency estimation based on accelerometer data, or the like. In such applications, the physiological data would be inputted and sequential beats, or intervals, detected as described herein with respect to ECG data. Accordingly, a person having ordinary skill in the art will understand in view of the present disclosure how to utilize the disclosed method of heart rate estimation in order to conduct period estimation in other forms of physiologic data or other patient monitoring data.

Following generation of a beat array at step 56, the beat intervals therein are sorted in order to generate a sorted beat array at step 58. For example, the beat intervals in the array may be sorted in ascending order, where the lowest interval duration is positioned first in the array and the greatest beat interval duration is positioned last in the sorted beat array. A weight array is then calculated at step 60 by applying a weight control parameter to each beat interval in the sorted beat array. The weight array includes a weight value for each beat interval, wherein the weight value is proportional to the corresponding beat interval value in the sorted beat array. Referring to the exemplary weight equation shown above, the weight value for each beat interval in the sorted beat array is calculated by raising each of the sorted beat intervals to the power $\lambda$.

A weighted median of the weight array is then calculated at step 62. Various methods of weighted median calculation are well-known and may be utilized. For example, the weighted median of the weight array may be identified based on a lower weighted median and/or an upper weighted median. For instance, the weighted median of the weight array identified at step 62 may be identified as the more recent one of the lower weighted median and the upper weighted median, where the more recent one is the beat interval occurring more recently in time. Alternatively, the weighted median may be determined based on an average of two elements, and the corresponding value in the sorted beat array may be identified likewise at step 64.

In order to avoid oscillations in the output, in certain embodiments, the T-median may be always computed as an average of two elements surrounding the identified weighted median point. For example, the T-median may be identified as the average of two beat intervals in the sorted beat array. When the weighted median falls between two beat interval values, the T-median may be calculated as an average of those surrounding elements. Namely, the T-median may be calculated as a mean of the preceding and succeeding beat intervals. Where the preceding and succeeding beat intervals are equal, the T-median may be calculated as the average of the beat intervals further preceding and succeeding those surrounding beat intervals, and so on such that the T-median is always computed as an average of two elements. An exemplary T-median calculation for exemplary beat interval data is provided below.

In certain embodiments (such as exemplified in FIGS. 6 and 10 and described herein), additional computation may be provided in order to adjust, or adapt, the weight control parameter based on the beat interval data. Additionally, where the heart rate (or other physiologic interval) significantly changes, the array window may be shortened in order to increase the reactivity of the T-median estimation. The array window is shortened only temporarily in order to increase the reactivity of the heart rate estimation and respond to a sustained change in heart rate. After shortening the array window, the window length is then increased back to its initial size—e.g., one interval value at a time. Thereby, the heart rate estimation returns the steadier, more filtered, estimation method that is less reactive to erroneous interval detections. Further explanation and examples of array window adjustment in order to shorten the delay and increase the reactivity of the T-median estimation are provided herein below.

The heart rate estimation is then determined at step 100 based on the T-median estimation. The steps for calculating the heart rate estimation will vary depending on the format of the beat interval data. For example, where the beat intervals are presented as a number of samples between two periodic elements, such as two R peaks, then the heart rate may be calculated as the sample frequency divided by the number of samples in the beat interval (multiplied by 60 in order to arrive at a beats-per-minute value). Alternatively, the beat intervals may be provided in time units, e.g., seconds, and the heart rate may be calculated accordingly.

The heart rate estimation may be calculated periodically, such as every second, or may be recalculated following each sequential beat detection. A T-median calculation example using exemplary beat interval data is provided below. For brevity, the example is provided using an array window of eight beat intervals. In other embodiments, a greater number of beat intervals may be used. In certain embodiments, it may be desirable to provide a default array window length of at least ten second so that the T-median estimation is not overly reactive to transient changes resulting from interference. To provide examples, the array window may be, for example, at least 12 seconds in length or at least 16 seconds in length. Alternatively, the array window duration may be generated based on numbers of sequential beat intervals, such as at eight beat intervals or ten beat intervals. As explained in more detail below, the default array window size may be shortened temporarily in order to speed up alignment of the T-median estimation with a sustained change in heart rate.

The following exemplifies the T-median estimate computation based on the exemplary beat intervals measured as a number of samples between two R-peaks at a sample frequency is 200 hertz. The exemplary beat array is the following:

$$r=[252\ 360\ 240\ 144\ 180\ 120\ 60\ 132] \quad (3)$$

A sorted beat array is generated by sorting the beat intervals in the beat array (3), which is provided by the following:

$$r_s=[60\ 120\ 132\ 144\ 180\ 240\ 252\ 360] \quad (4)$$

With an initial exemplary control parameter value $\lambda=0.3$, we get the weight vector w by computing $w=r_s^\lambda$, i.e., raising each element of r to power $\lambda$:

$$w=[3.4154\ 4.2049\ 4.3269\ 4.4413\ 4.7488\ 5.1768\ 5.2532\ 5.8464] \quad (5)$$

A weighted median of the weight array is then calculated by cumulatively summing the weight values in the weight array. The cumulative sum of w is:

$$w_\Sigma=[3.4154\ 7.6203\ 11.9472\ 16.3885\ 21.1372\ 26.3141\ 31.5672\ 37.4136] \quad (6)$$

The 50% point of the cumulative sum $w_\Sigma$ is 37.4136/2=18.7068. The first element covers the cumulative weight from 0 to 3.4154, second covers from 3.4154 to 7.6203, and the 50% point is reached by the $5^{th}$ element. Here, the fifth beat interval (the higher weighted median) is the more recent one of the higher and lower medians. Thus, the T-median value is the value of the $5^{th}$ element in the sorted list (6) which is 180. Since the inputs are RR intervals with unit $\frac{1}{200}$ seconds, the final heart rate is computed from the T-median output as HR=200/180*60=66.7 bpm.

Figure 6:
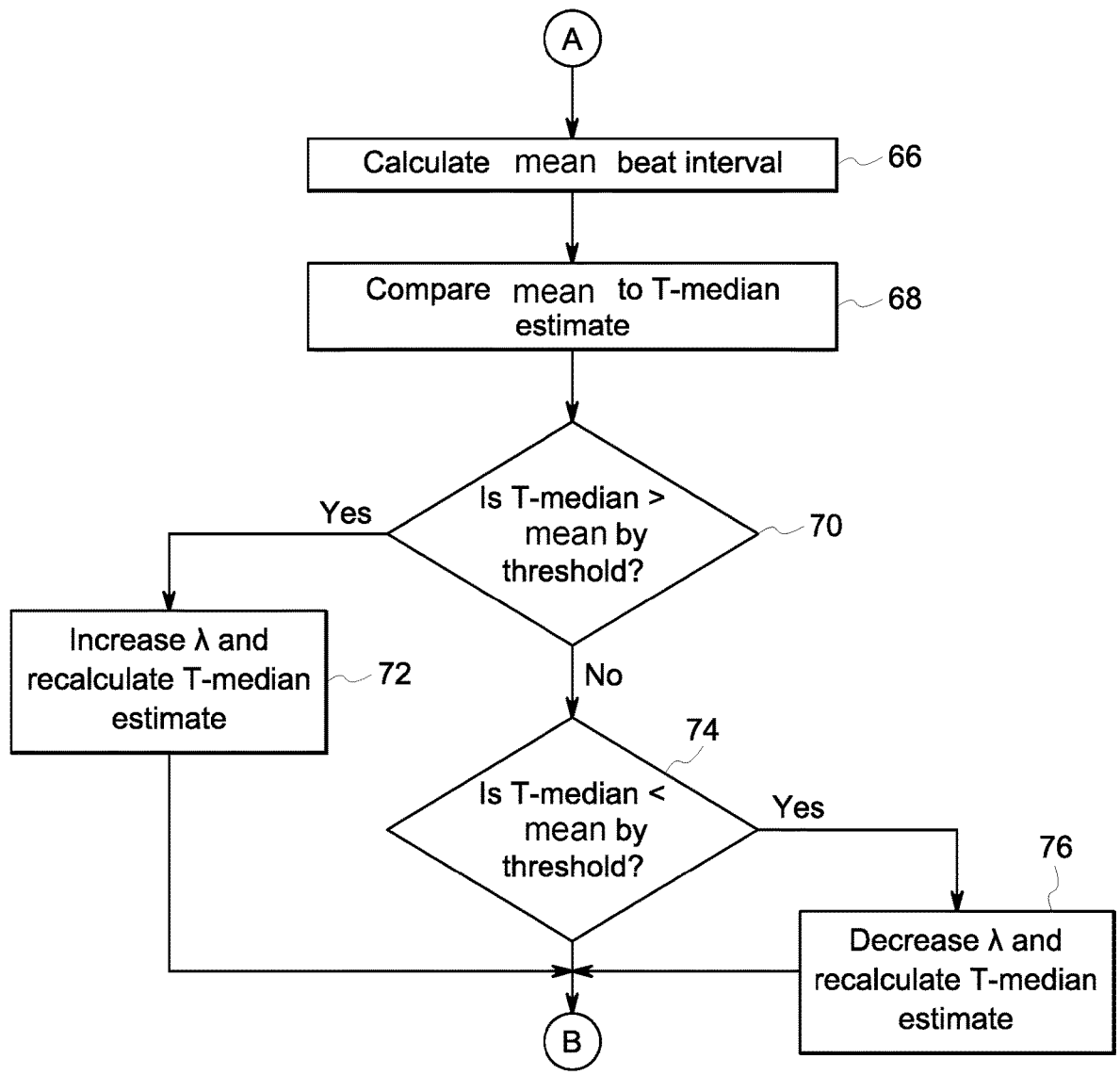
FIG. 6 is a flow chart illustrating a method of heart rate estimation according to another embodiment of the present disclosure.

The T-median calculation is adapted based on the content of the beat array by adjust the weight control parameter $\lambda$. One embodiment of such weight control parameter adjustment is depicted at FIG. 6, which corresponds to the weight control formula (2) presented above. In the example, a mean beat interval is calculated at step 66, which is the mean of the beat intervals in the beat array. The mean beat interval is then compared to the previously-calculated T-median estimate at step 68. If the T-median estimate is greater than the mean beat interval by a threshold at step 70, then the weight control parameter $\lambda$ is increased. If the T-median estimate is less than the mean beat interval by a threshold amount at step 74, then the weight control parameter is decreased. The threshold for changing the weight control parameter may be relatively small, such as two percent or five percent of the T-median estimate or the mean beat interval. In other embodiments, the threshold may be zero, requiring that the weight control parameter be adjusted if the T-median estimate is not exactly equal to the mean beat interval.

Where the T-median is sufficiently greater than the mean beat interval, then the control parameter $\lambda$ is increased at step 72 and the T-median estimate is recalculated accordingly. For example, the weight control parameter $\lambda$ may be adjusted proportionately to the previously-calculated T-median value and the mean beat interval. Conversely, where the previously-calculated T-median value is sufficiently less than the mean beat interval, then the control parameter $\lambda$ is decreased at step 76 and the T-median estimate is recalculated using that new control parameter value. The control parameter $\lambda$ may be adjusted, for example, proportionately to the difference between the previously-calculated T-median estimate and the mean beat interval.

Figure 7A:
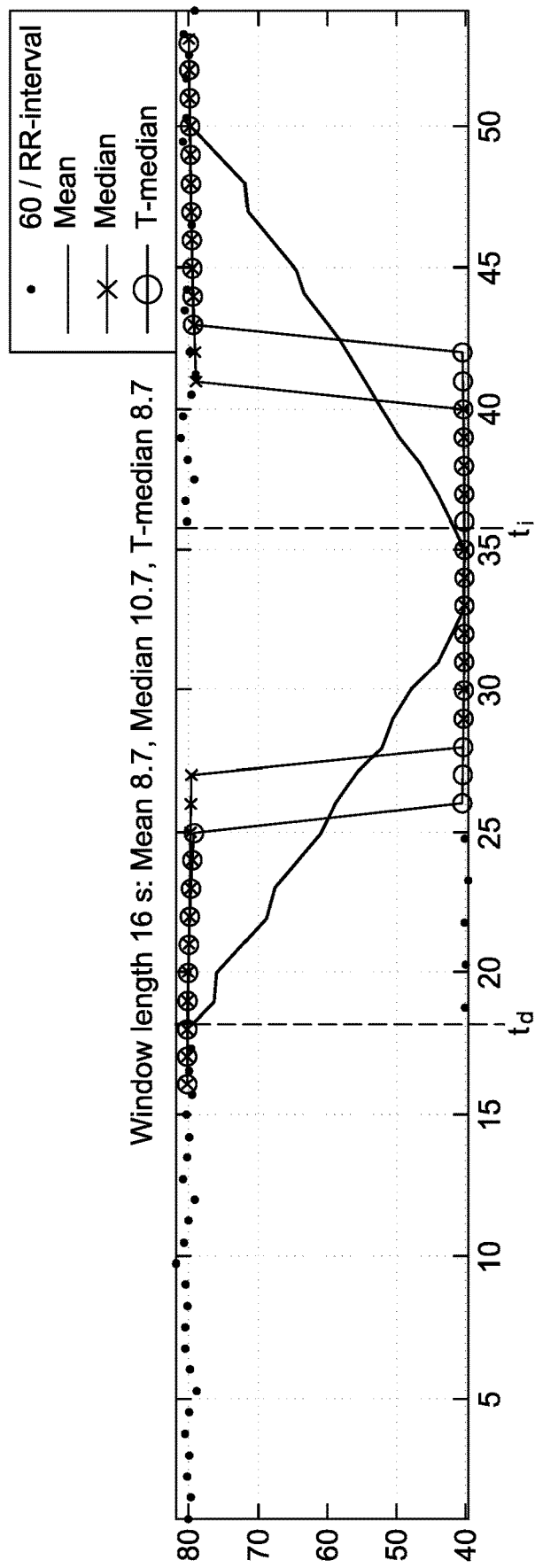
FIGS. 7A-7C are graphs comparing a standard median heart rate calculation to the disclosed time-based weighted median calculation for a given data set, using a window length of 16 seconds.
Figure 7B:
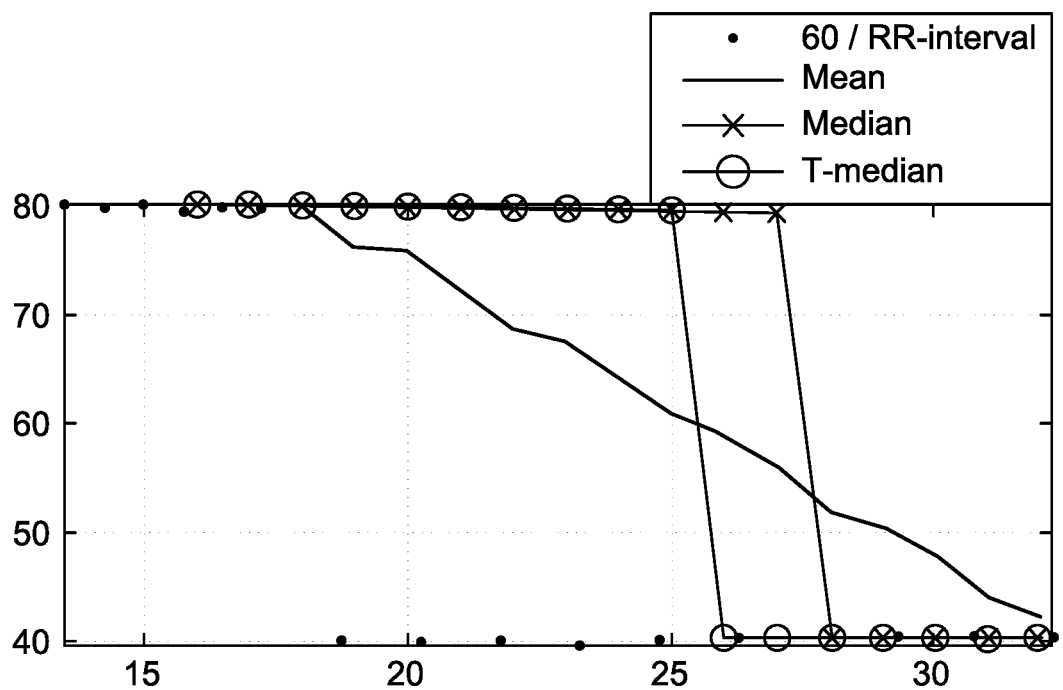
Figure 7C:
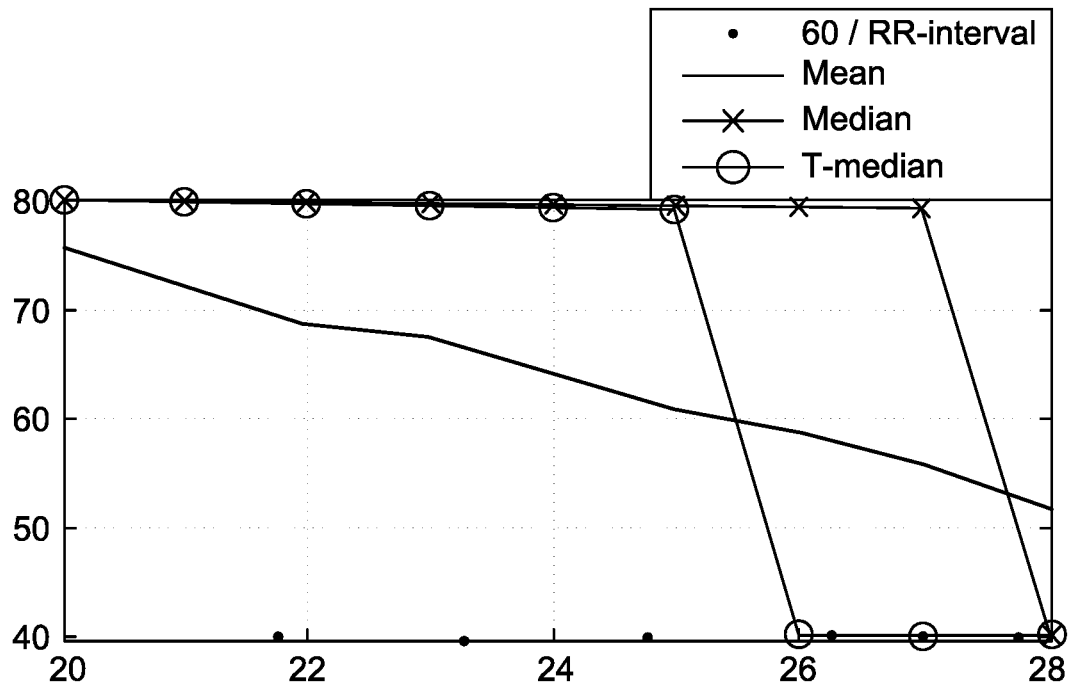

FIGS. 7A-7C are graphs demonstrating the disclosed T-median calculation compared with the standard median calculation and the mean calculation for the same ECG data as depicted in FIGS. 2A-2C. As demonstrated in FIGS. 7A-7C, the T-median estimation of the heart rate is less biased than the standard median calculation. Namely, the T-median estimation is more responsive to decreases in heart rate and less responsive to increases in heart rate than the standard median estimation. In particular, the weight control parameter $\lambda$ is adjusted so that the average of T-median estimates equals the average of mean beat intervals (see also FIG. 9). Thus, as listed at the top of FIG. 7A, where an array window of 16 seconds is used, the mean and the average T-median are equal, whereas the average median heart rate is higher.

Figure 8A:
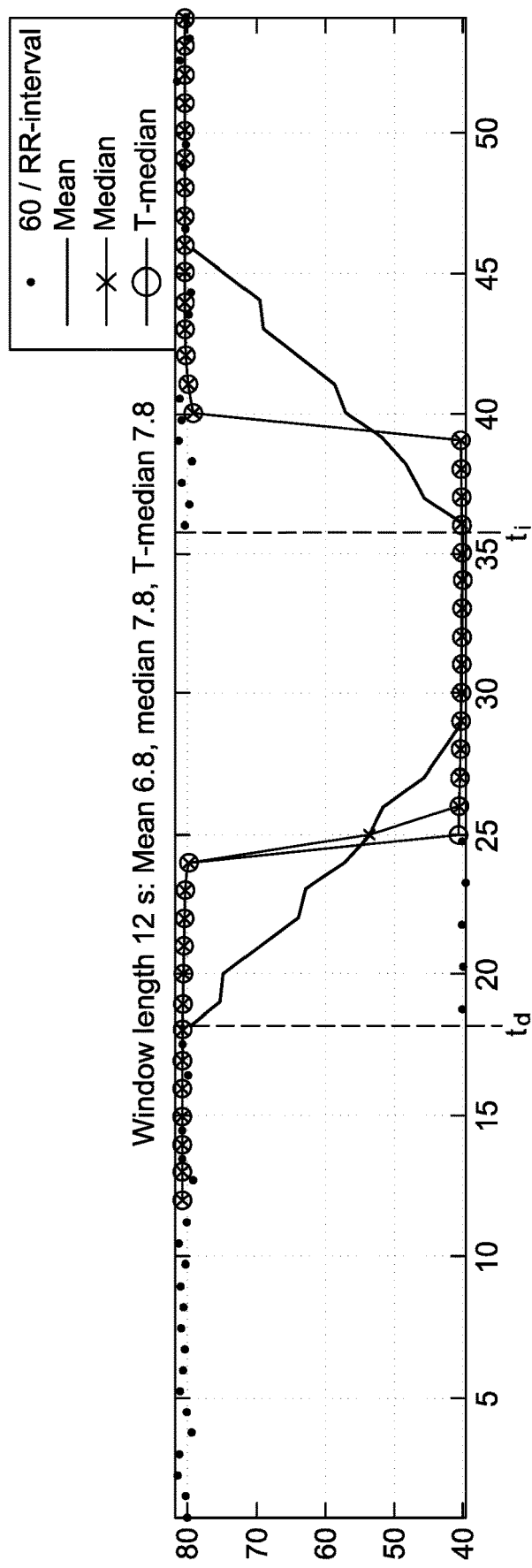
FIGS. 8A-8C are graphs comparing a standard median heart rate calculation to the disclosed time-based weighted median calculation for a given data set, using a window length of 12 seconds.
Figure 8B:
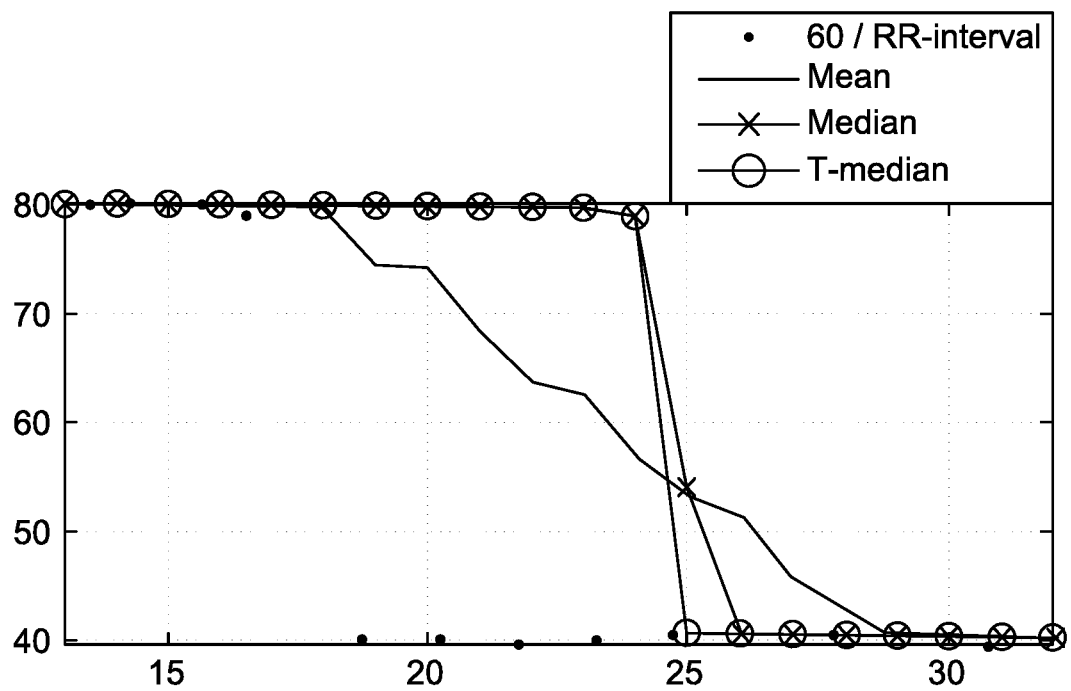
Figure 8C:
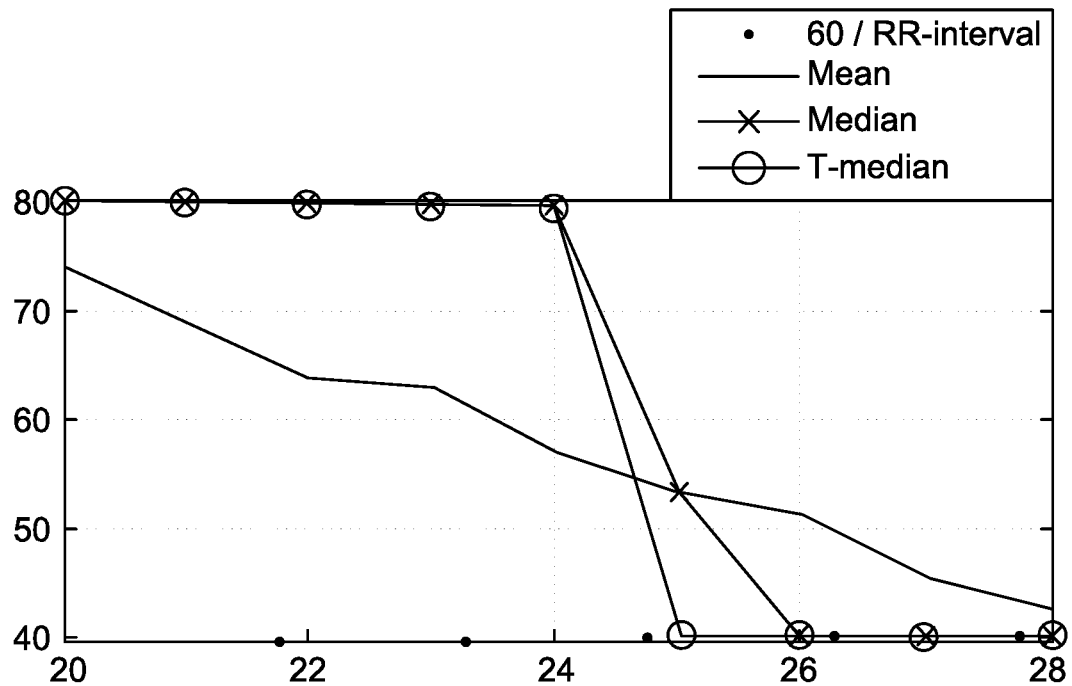

The graphs in FIGS. 8A-8C demonstrate a comparison of the T-median and standard mean heart rate estimations for the same heart rate data, only using an array window length of 12 seconds as opposed to an array window length of 16 seconds shown in FIGS. 7A-7C. As shown in the example, the estimation calculations by both of the T-median and the standard median are more responsive when a window length of 12 seconds is used as opposed to a window length of 16 seconds. The T-median estimation is more responsive to the heart rate decrease from 80 to 40 than the standard median calculation, but the T-median estimation is equally responsive as the median estimation to a heart rate increase. In order to maximize responsiveness to a sustained change in heart rate, the array window may be temporarily shortened, and examples for such T-median estimation speedup are provided below.

Figure 9:
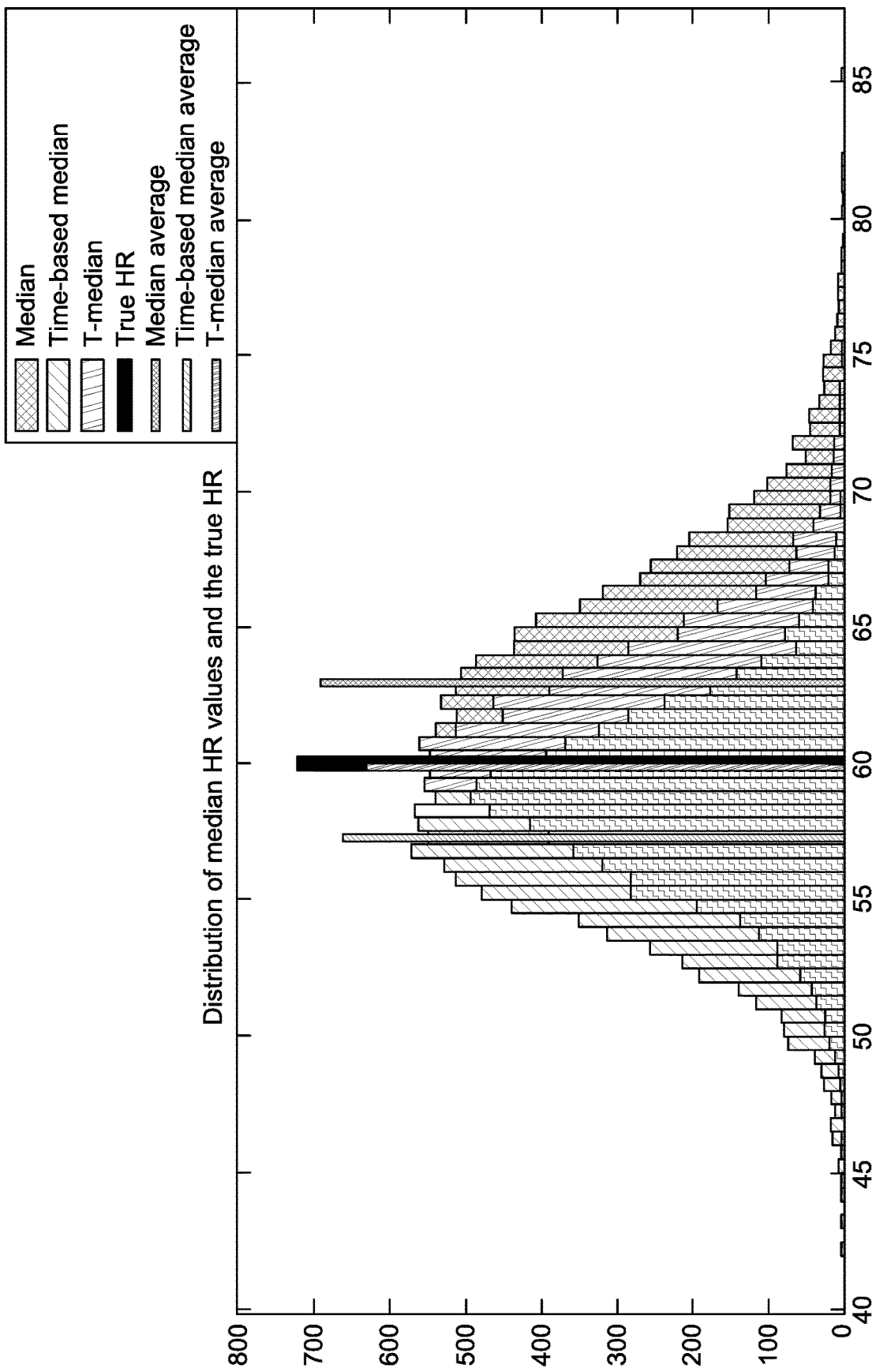
FIG. 9 is a graph comparing heart rate calculation using the disclosed time-based weighted median method to heart rate calculation results using a standard median method and using a time-based median method.

FIG. 9 shows a comparative distribution of heart rate estimations calculated by the standard median, time-based median, and T-median methods. As shown, the average T-median is approximately equal to the true heart rate, whereas the average standard median and the average time-median values are biased, where the averages are computed as means. As described above, in certain embodiments a speedup calculation may be utilized to shorten the array window length in order to increase responsiveness of the T-median estimation to a sustained heart rate change (or change in the interval for whatever physiologic data for which the disclosed periodic estimation may be utilized)—referred to herein as the "fast T-median estimate". When compared to a standard median calculation, the T-median with a sufficiently long array window is faster to react to a drop in heart rate, but is slower to react to a rise in heart rate. This reaction time can be shortened by studying the original position of the beat intervals around the one that is to be selected. Where the RR-interval is increasing, samples after the initial T-median calculation in the sorted beat array are studied. Conversely, where the beat interval is decreasing, samples before the initial T-median estimation in the sorted list of beat intervals are studied.

Figure 10:
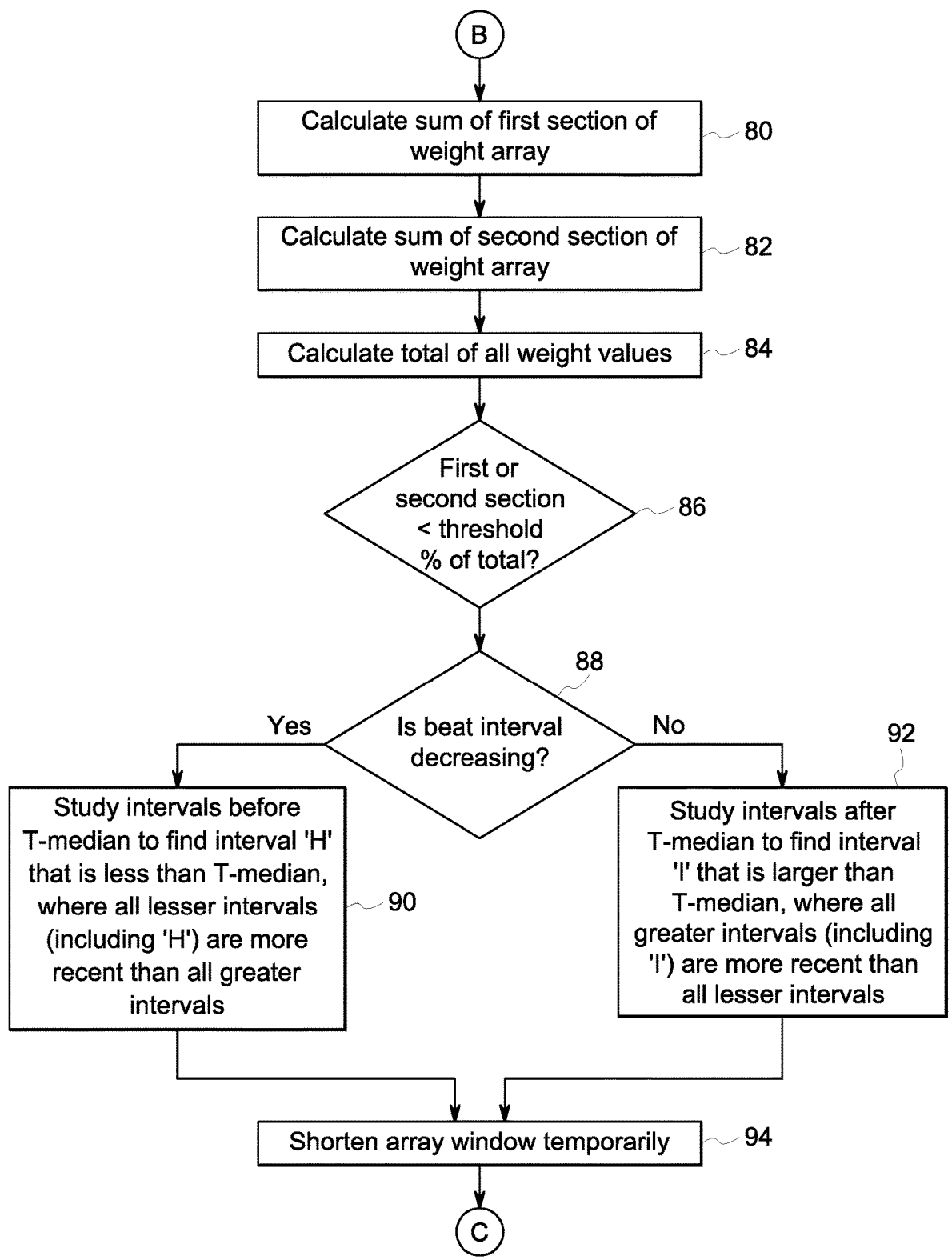
FIG. 10 is a flow chart illustrating a method of heart rate estimation according to another embodiment of the present disclosure.
Figure 11A:
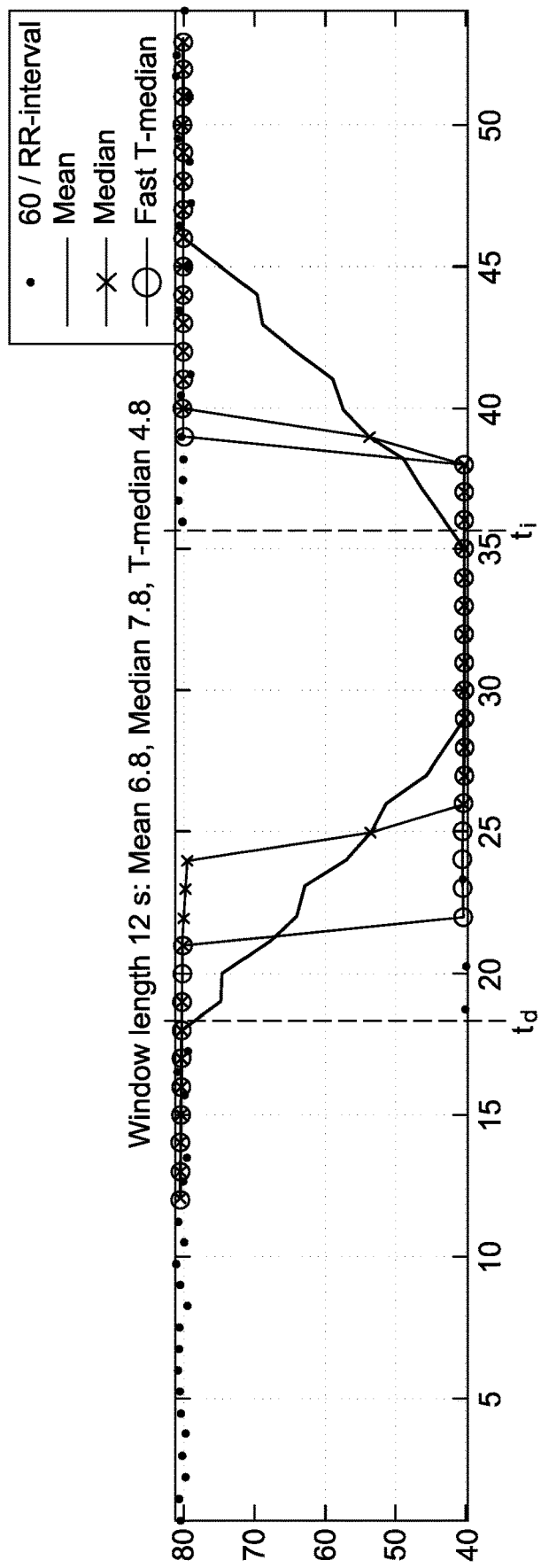
FIGS. 11A-11C are graphs showing another embodiment of an adaptive time-based weighted median estimation of heart rate compared to a standard median calculation for the given data set.
Figure 11B:
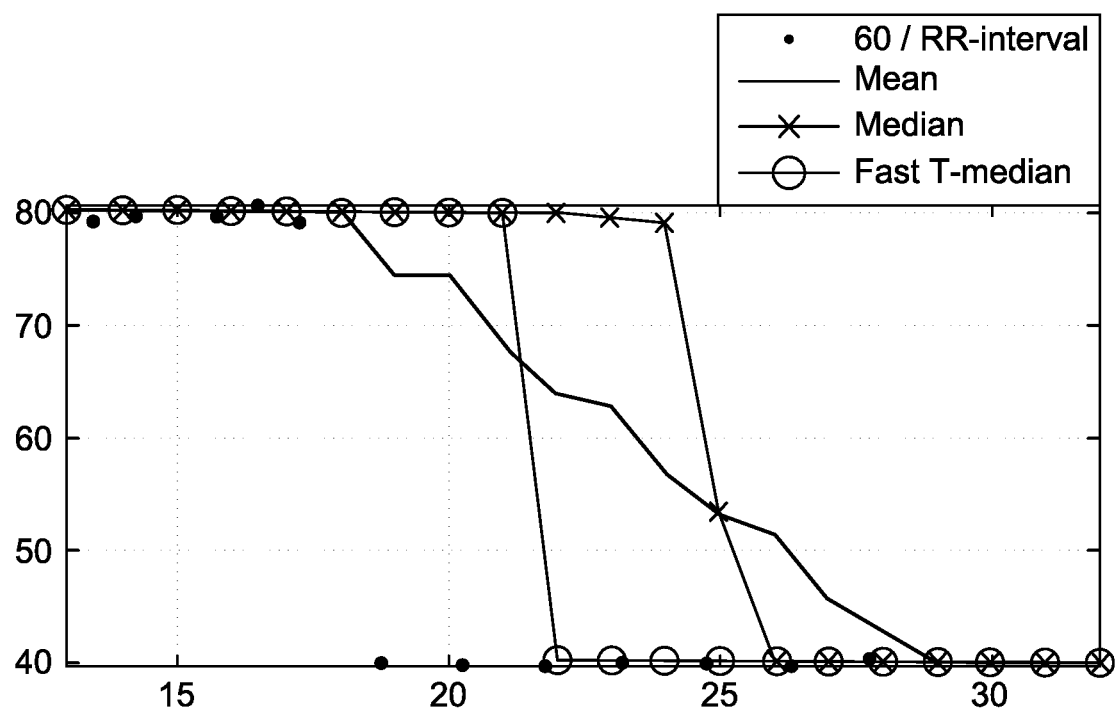
Figure 11C:
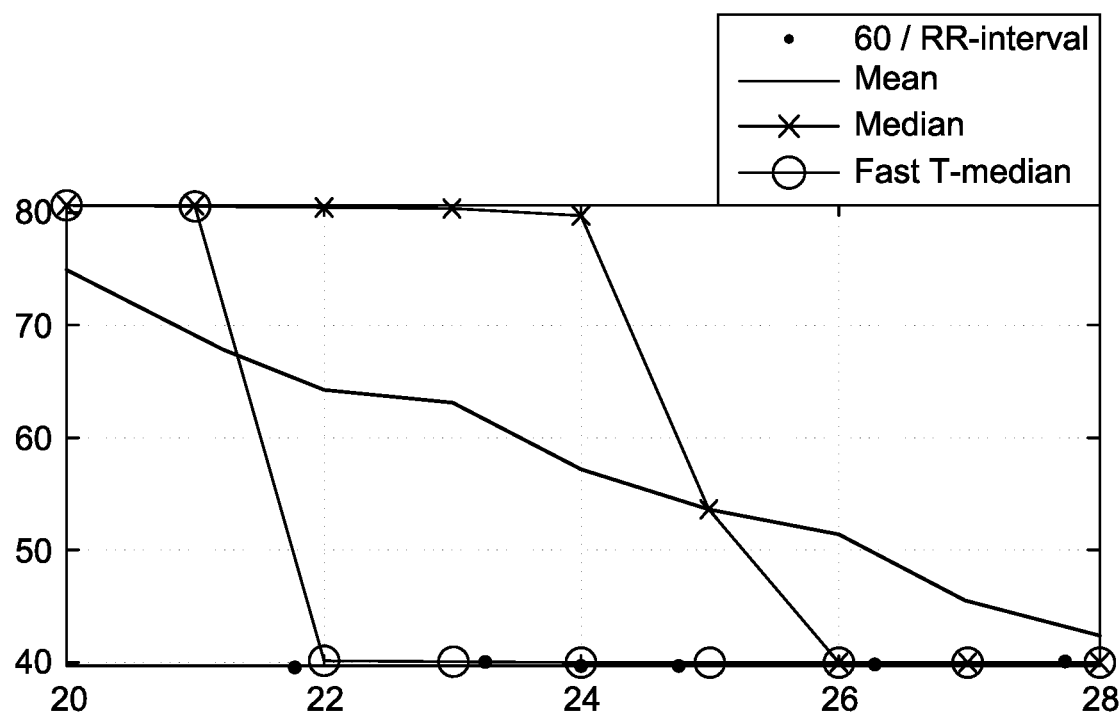

FIG. 10 depicts one example of a fast T-median calculation, where steps are executed to locate appropriate beat intervals for increasing the responsiveness of the T-median estimation. In the depicted example, the arrays on either side of the initial T-median calculation are summed. Thus, a sum of the first section of the weight array is calculated at step 80, wherein the first section includes all weight values in the weight array (which is based on the sorted beat array) up to the weighted median element identified as described above. A second section of the array containing those weight values greater than the weighted median may also be summed, such that a sum of the second section of the weight array is calculated at step 82. A total of all weight values in the weight array is calculated at step 84. At step 86, instructions are executed to determine whether the first or second sections of the weight array are greater than a threshold percentage of the sum total of all weight values. For example, if the shorter end of the weight array divided in two by the median element is less than 20% of the sum of all weight values in the weight array, then it may be determined that a sustained change in heart rate has occurred and that a fast T-median calculation is necessary such that the T-median estimation can quickly reflect the change in heart rate.

The logic for adjusting the array window will depend on whether the heart rate is decreasing or increasing. If the beat interval is decreasing at step 88, then steps are executed to study the beat intervals before the previously-identified T-median to find a beat interval, labeled here as beat interval "H" that should be selected as the T-median element for the amended fast T-median estimation. Candidate elements, or beat intervals, before the T-median element are examined at step 90 to find the interval H that is less than the initially-calculated T-median, and where all beat intervals preceding the new T-median element H are more recent than all beat intervals after the beat interval H (i.e. more recent than all beat intervals with a larger magnitude). Thus, where the beat interval is decreasing, and thus the heart rate is increasing, the system locates all elements for which following are true:

I. The element must be more recent than the current T-median element.
II. The element value must be closer to the latest input value than what the current T-median value is.
III. The element must be an output of some T-median computed with a shorter window length.

Conversely, if the beat interval is increasing at step 88, and thus the heart rate is decreasing, then instructions are executed as represented at step 92 to study the beat intervals after the T-median in the sorted beat array to find an interval "I" that satisfies the above-listed conditions. Namely, a beat interval I is located that is larger than the previously-determined T-median estimation, where all greater beat interval values (including beat interval I itself) are more recent than all lesser beat intervals (e.g. all intervals preceding I in the sorted beat array). Once these intervals are determined, the shortened beat array having the shortened array window is outputted at step 94 from which the heart rate estimation is determined.

By studying only such elements, the system ensures that an array window exists that is shorter than the previous-implemented array window and produces an accurate T-median estimation using fewer data points. Thereby, the older data, presumably reflecting the previous heart rate instead of the current heart rate, can be more quickly "forgotten" in the estimation calculation. Thereafter, the array window can be incrementally increased back up to the normal, predetermined length. For example, one array position may be added for each calculation iteration following the fast T-median estimation calculation.

The speedup calculation for the fast T-median calculation will be illustrated using the beat array (3). The beat array (3) and corresponding age array of the "ages" of each beat interval are provided as follows:

$$r = [252\ 360\ 240\ 144\ 180\ 120\ 60\ 132] \quad (3)$$

$$\text{Age array} = [0\ 1\ 2\ 3\ 4\ 5\ 6\ 7] \quad (7)$$

where the most recent element is given first. After sorting the data, the following sorted beat array (4) and corresponding age array are presented as follows $$r_s = [60\ 120\ 132\ 144\ 180\ 240\ 252\ 360] \quad (4)$$

$$\text{Sorted age array} = [6\ 5\ 7\ 3\ 4\ 2\ 0\ 1] \quad (8)$$

As described above, the T-median estimation with the weight control parameter $\lambda=0.3$, which gives the fifth element in the sorted array as the T-median element, i.e., $r_T=5$ and $m_T=180$.

Instead of going through all various lengths of median windows with an exhaustive search routine for the speedup calculation, arrays (4) and (8) are searched for suitable speedup output elements. With the example data (3), as the age of the 5th element in the sorted age array (8), $a_5=4$, is larger than the age of the last element, $a_5=1$, the RR value is considered to increase. To find out the possible speedup candidate elements, we search for the elements that divide the age array to old and recent elements, i.e., all the elements before the dividing element in array (4) must be older than the dividing element itself and the elements succeeding the dividing element. Such elements are Fourth element: divides the array (8) into [6 5 7] and [3 4 2 0 1]
Sixth element: divides the array (8) into [6 5 7 3 4] and [2 0 1]
Seventh element: divides the array (8) into [6 5 7 3 4 2] and [0 1]

These elements are searched by computing the cumulative maximum value starting from the end of the age array, subtracting from it the cumulative minimum starting from the beginning of the age array, and searching for elements −1 from the result.

All of the three listed candidates are more recent than the current T-median element with age $a_5=4$, and thus all of them provide speedup in sense of moving the selected T-median element forward in time. Next, the speedup provided by each of these three elements is examined in sense of the T-median value. If the fourth element, $a_4=3$, would get selected, the relative speedup in sense of a change in the T-median value would be $m_4/m_5=144/180=0.8$. For the other two elements, the change ratios are $m_6/m_5=240/180=1.33$ and $m_7/m_5=252/180=1.4$. As the values increase, i.e., the most recent value is larger than the older ones, in the speedup routine one is trying to increase the output of the T-median. The larger the speedup in the sense of the change of the T-median value, the more shortening of the median window can be justified—i.e., the more the selection may be moved from the default location. In here, fourth element does not increase the value, so choosing that one cannot be justified. Thus, only the sixth and seventh elements are left.

The weights associated with the data values in array (3) with $\lambda=0.3$ are shown in array (9), $$[3.4154\ 4.2049\ 4.3269\ 4.4413\ 4.7488\ 5.1768\ 5.2532\ 5.8464] \quad (9)$$

The minimum required weight remaining on the right-hand side of the selected speedup element in array (9) is determined as a function of the speedup ratio provided by that element—i.e., the relative change produced by selecting that element instead of the 50% T-median element. With the current default parameter set, ratio 1.33 of the sixth element justifies a speedup that leaves 30% of the total weight to the elements 6, 7, and 8; and ratio 1.4 of the seventh element justifies leaving only 26% of the weight to the elements 7 and 8. By dividing the cumulative weight array corresponding to array (9) with the total weight and by multiplying the result with 100%, the following array results:

$$[9.13\%\ 20.37\%\ 31.93\%\ 43.80\%\ 56.50\%\ 70.33\%\ 84.37\%\ 100.00\%] \quad (10)$$

From the weight ratio array above, it can be seen that 50% of the total weight is reached at the point of the fifth element, which was thus selected as the default T-median element. The sixth element leaves 100%−56.50%=44.50% of the weight for the succeeding elements and the element itself, and as 44% is larger than 30%, that element is considered as a valid speedup candidate. The seventh element leaves 100%−70.33%=29.67%, that is larger than 26%, and thus also that element is considered as valid speedup candidate.

As there is more than one suitable candidate, the oldest one (most conservative choice) is selected: in this case, it is the sixth element, $m_6=240$. After choosing the speedup element, solve for the length of the T-median that would have produced this element as the T-median value according to the 50% rule. By computing the cumulative weight starting from the most recent element until the 50% point is reached in the point of the selected element, the length of the shortened T-median is found to be 5. In other words, by selecting the sixth element in the sorted array, the same answer is produced that would have been produced by taking the T-median from the following array:

$$[252\ 360\ 240\ 144\ 180] \quad (11)$$

That is, the answer would have been the same if we would have computed the T-median after leaving the three oldest elements out. This is as the cumulative relative weight array corresponding to (11) with $\lambda=0.3$ is $$[17.44\ 36.09\ 56.41\ 77.04\ 100.00] \quad (12)$$

and the third element is at the 50% point. The timestamp of the oldest element in the "imaginary" T-median window above is kept in the memory, and all elements with smaller timestamp values than that, i.e., the elements older than that, are dropped when processing the succeeding median windows. That is, if the next input value is 200, and the T-median window thus covers the following samples:

$$[200\ 252\ 360\ 240\ 144\ 180\ 120\ 60\ 132] \quad (13)$$

Elements older than the oldest one in the array (11) are dropped, thus leaving the next T-median to be computed from the following:

$$[200\ 252\ 360\ 240\ 144\ 180] \quad (14)$$

The case of decreasing input value is handled in similar manner.

Graphs 11A-11C show comparative heart rate estimations using the standard median and the disclosed fast T-median calculations using a window length of 12 seconds based on the same heart rate data shown in the previous graphs, including FIGS. 8A-8C. By comparing graphs 11A-11C to graphs 8A-8C, it can be seen that the fast T-median calculation provides a more immediate reflection of the change in heart rate from 80 to 40, where the fast T-median estimation responds to the decrease in heart rate from 80 to 40 in approximately four seconds, which is significantly faster than the T-median estimation using the full array window and also much faster than the heart rate estimation given by the standard median estimation.

Figure 12:
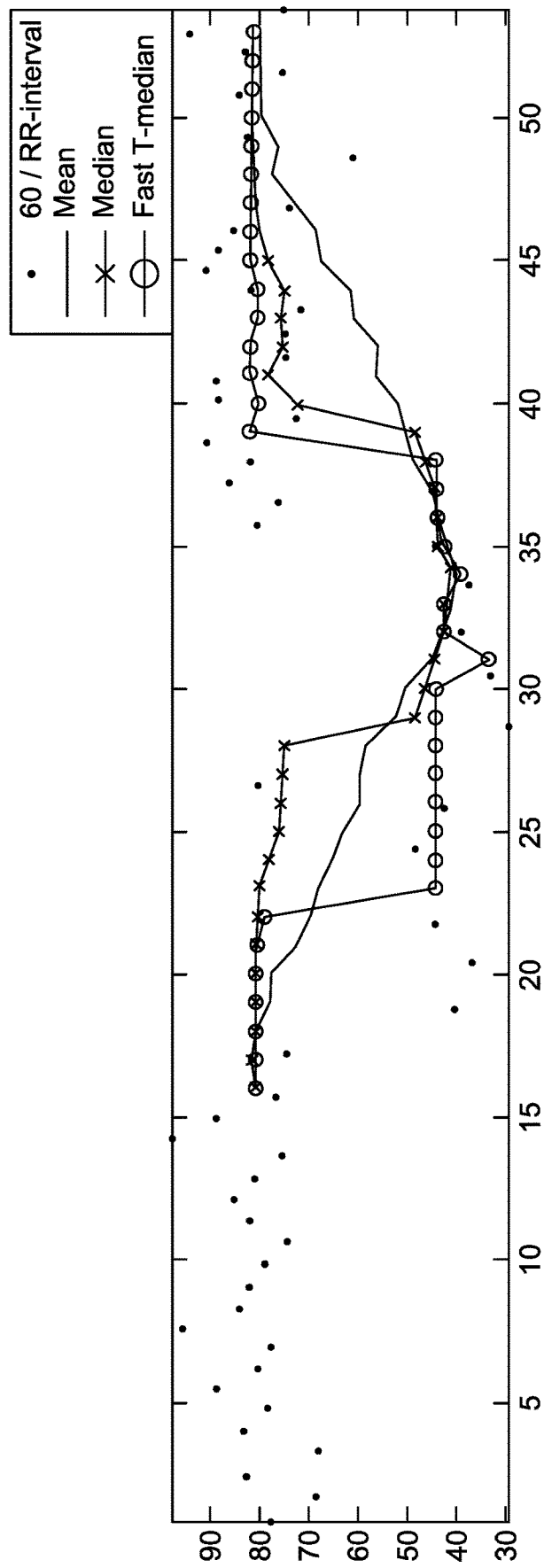
FIG. 12 is a graph comparing the adaptive time-based weighted median heart rate calculation to a standard median heart rate calculation for another, nosier data set.

The graph at FIG. 12 provides additional comparative data based on a different set of heart rate measurements. The data depicted in FIG. 12 is noisy compared to the data shown in the previous graphs, which demonstrates the performance of the fast T-median estimation described herein. In certain embodiments, in order to avoid unwanted side-effects caused by moving the median point forward unnecessarily, the median point may be moved (i.e. the fast T-median estimation utilized) only if the fast T-median estimate significantly differs from the previously-determined T-median estimate. For example, the fast T-median estimate may be utilized where it differs from the original T-median value by at least 20%. Thereby, the use of the fast T-median estimate may be restricted only to situations of sustained heart rate change in order to avoid reacting to noise and individual outliers.

After moving the median point forward in time to decrease the lag and speed up the responsiveness, the oldest timestamp of the original beat array has to be remembered by the system—i.e., the oldest value in the beat array that would have produced the same output as the one achieved by the fast T-median estimate. The older samples must then be "dropped" when computing succeeding T-median values. Thus, the fast T-median estimation is computationally burdensome.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A computer-implemented method of heart rate estimation for patient monitoring, the method comprising:
   receiving heart beat data at a processing system of a patient monitor;
   at the processing system of the patient monitor;
   detecting sequential beats within the heart beat data and identifying a beat interval of each sequential beat;
   generating a beat array containing the beat intervals of the sequential beats within an array window;
   sorting the beat array based on the beat intervals of the sequential beats to generate a sorted beat array;
   calculating a weight array by applying a weight control parameter to each beat interval in the sorted beat array, wherein the weight array includes a weight value for each beat interval that is proportional to a corresponding beat interval value in the sorted beat array;
   calculating a weighted median based on the weight array;
   determining a heart rate estimation for the array window based on the weighted median and the sorted beat array; and
   outputting the heart rate estimation.

2. The method of claim 1, wherein each weight value in the weight array is calculated as $r^\lambda$, where r is the beat interval and $\lambda$ is the weight control parameter, and wherein $0<=\lambda<=1$.

3. The method of claim 2, further comprising increasing the weight control parameter when the weighted median is greater than an average beat interval and decreasing the weight control parameter when the weighted median is less than the average beat interval.

4. The method of claim 3, further comprising adjusting the weight control parameter by an amount proportional to a difference between the weighted median and the average beat interval.

5. The method of claim 1, further comprising adjusting the weight control parameter based on one or more of the beat intervals in the array window.

6. The method of claim 1, wherein calculating the weighted median includes determining a lower weighted median of the weight array and determining an upper weighted median of the weight array, wherein the heart rate estimation is determined based on at least one of the lower weighted median and the upper weighted median.

7. The method of claim 6, wherein the weighted median is equal to a more recent one of the lower weighted median and the upper weighted median.

8. The method of claim 6, wherein the heart rate estimation is determined based on an average of the beat intervals in the sorted beat array associated with the lower weighted median and the upper weighted median in the weight array.

9. The method of claim 8, wherein, when the lower weighted median is equal to the upper weighted median, then the heart rate estimation is determined based on an average of the beat intervals in the sorted beat array associated with the weight value preceding the lower weighted median and the weight value succeeding the upper weighted median in the weight array.

10. The method of claim 1, further comprising detecting a threshold change in the beat intervals across the sorted beat array, and then shortening a length of the array window.

11. The method of claim 10, wherein the threshold change is one of a sum of the weight values preceding the weighted median in the weight array or a sum of the beat intervals succeeding the weighted median in the weight array are less than 20% of a sum of all weight values in the weight array.

12. The method of claim 1, wherein the array window is defined by one of a predetermined time interval or a predetermined number of sequential beats.

13. The method of claim 1, wherein the sorted beat array contains the beat intervals sorted in ascending order such that a shortest beat interval is first and a longest beat interval is last.

14. The method of claim 1, wherein detecting sequential heart beats includes detecting sequential R-R intervals and wherein the beat interval is one of a time interval between two R peaks and a number of samples between two R peaks.

15. A patient monitoring system for monitoring heart rate, the system comprising:
at least two ECG electrodes communicatively connected to a patient monitor and configured to record at least one lead of heart beat data from a patient, the patient monitor configured to determine a heart rate estimation based on the heart beat data and display the heart rate estimation on a display;
a processing system configured to:
generate a beat array containing beat intervals of sequential beats within an array window of the heart beat data;
sort the beat array based on the beat intervals of the sequential beats to generate a sorted beat array;
calculate a weight array by applying a weight control parameter to each beat interval in the sorted beat array, wherein the weight array includes a weight value for each beat interval that is proportional to a corresponding beat interval value in the sorted beat array;
calculate a weighted median based on the weight array;
determine the heart rate estimation for the array window based on the weighted median and the sorted beat array; and
display the heart rate estimation on the display.

16. The system of claim 15, wherein each weight value in the weight array is calculated as $r^\lambda$, where r is the beat interval and $\lambda$ is the weight control parameter, and wherein $0<=\lambda<=1$.

17. The system of claim 16, wherein the processing system is further configured to increase the weight control parameter when the weighted median is greater than an average beat interval and decrease the weight control parameter when the weighted median is less than the average beat interval.

18. The system of claim 15, wherein the processing system is further configured to adjust the weight control parameter based on one or more of the beat intervals in the array window.

19. The system of claim 15, wherein the processing system is further configured to detect a threshold change in the beat intervals across the sorted beat array, and then shortening a length of the array window.

20. The system of claim 19, wherein the threshold change is one of a sum of the weight values preceding the weighted median in the weight array or a sum of the beat intervals succeeding the weighted median in the weight array are less than 20% of the sum of all weight values in the weight array.

21. The method of claim 1, wherein outputting the heart rate estimation includes controlling a display associated with the patient monitor to display the heart rate estimation.

* * * * *